US012290807B2

(12) United States Patent
Garstecki et al.

(10) Patent No.: US 12,290,807 B2
(45) Date of Patent: May 6, 2025

(54) INCUBATION WELL WITH AN UNVENTED GAS CAVITY FOR USE IN A MICROFLUIDIC CHIP

(71) Applicant: BACTEROMIC SP. z O.O., Warsaw (PL)

(72) Inventors: Piotr Garstecki, Warsaw (PL); Jaroslaw Ziólkowski, Konstantynów Lódzki (PL); Piotr Knap, Hrubieszów (PL)

(73) Assignee: BACTEROMIC SP. Z O.O., Warsaw (PL)

( * ) Notice: Subject to any disclaimer, the term of this patent is extended or adjusted under 35 U.S.C. 154(b) by 864 days.

(21) Appl. No.: 17/043,449

(22) PCT Filed: Mar. 29, 2019

(86) PCT No.: PCT/EP2019/058045
§ 371 (c)(1),
(2) Date: Sep. 29, 2020

(87) PCT Pub. No.: WO2019/185885
PCT Pub. Date: Oct. 3, 2019

(65) Prior Publication Data
US 2021/0023553 A1    Jan. 28, 2021

(30) Foreign Application Priority Data

Mar. 30, 2018  (PL) .......................................... 425107
Aug. 17, 2018  (EP) ..................................... 18189593

(51) Int. Cl.
*B01L 3/00*     (2006.01)
*C12M 1/00*    (2006.01)
(Continued)

(52) U.S. Cl.
CPC .......... *B01L 3/5027* (2013.01); *C12M 23/12* (2013.01); *C12M 23/16* (2013.01); *C12M 23/22* (2013.01);
(Continued)

(58) Field of Classification Search
CPC .......... B01L 3/5027; B01L 2200/0647; B01L 2300/0864; C12M 23/12; C12M 23/16; C12M 23/22; C12M 23/34; C12M 41/24
See application file for complete search history.

(56) References Cited

U.S. PATENT DOCUMENTS 4,018,652 A    4/1977 Lanham et al.
4,318,994 A    3/1982 Meyer et al.
(Continued)

FOREIGN PATENT DOCUMENTS

AU    2009270821 B2    1/2010
CN    101545901 A    9/2009
(Continued)

OTHER PUBLICATIONS

Somaweera, et al., A Review of Chemical Gradient Systems for Cell Analysis, Systems for Cell Analysis, Analytica Chimica Acta, 2016, pp. 1-47.
(Continued)

*Primary Examiner* — Liban M Hassan
(74) *Attorney, Agent, or Firm* — FisherBroyles, LLP; Ronni S. Jillions (57) ABSTRACT

An incubation segment in a microfluidic chip for microbiological assays, wherein said incubation segment is formed in a substrate with an upper major face and a lower major face, said segment includes an incubation well, an inlet channel through which a sample may be inputted into said incubation well, and a gas cavity connected to said incubation well by a microfluidic communication channel, wherein said gas
(Continued)

cavity is unvented and the base of the gas cavity is connected to the base of the incubation well by the communication channel.

25 Claims, 5 Drawing Sheets

(51) Int. Cl.
    *C12M 1/02*     (2006.01)
    *C12M 1/32*     (2006.01)
    *C12M 3/06*     (2006.01)

(52) U.S. Cl.
    CPC ............ *C12M 23/34* (2013.01); *C12M 41/24* (2013.01); *B01L 2200/0647* (2013.01); *B01L 2300/0864* (2013.01)

(56) References Cited

U.S. PATENT DOCUMENTS

| | | | |
|---|---|---|---|
| 5,744,366 A * | 4/1998 | Kricka | B01L 7/52 436/63 |
| 6,627,406 B1 | 9/2003 | Singh et al. | |
| RE42,882 E | 11/2011 | Kearney | |
| 2002/0001848 A1 * | 1/2002 | Bedingham | B01L 3/5025 436/180 |
| 2002/0119561 A1 | 8/2002 | Farina et al. | |
| 2003/0152994 A1 | 8/2003 | Woudenberg et al. | |
| 2004/0219732 A1 | 11/2004 | Burns et al. | |
| 2008/0257754 A1 | 10/2008 | Pugia et al. | |
| 2009/0155128 A1 | 6/2009 | Peters | |
| 2009/0181411 A1 | 7/2009 | Battrell et al. | |
| 2010/0240051 A1 | 9/2010 | Wang et al. | |
| 2010/0307595 A1 * | 12/2010 | Mark | G01F 13/00 137/1 |
| 2011/0020918 A1 | 1/2011 | Nassef et al. | |
| 2012/0088263 A1 | 4/2012 | Bruno et al. | |
| 2013/0065280 A1 | 3/2013 | Park et al. | |
| 2015/0238960 A1 | 8/2015 | Hong et al. | |
| 2016/0354777 A1 | 12/2016 | Chiu et al. | |
| 2017/0021352 A1 * | 1/2017 | Jiao | B01L 3/502746 |
| 2017/0029871 A1 | 2/2017 | Ying et al. | |

FOREIGN PATENT DOCUMENTS

| | | |
|---|---|---|
| CN | 103154744 A | 6/2013 |
| CN | 106676004 A | 5/2017 |
| EP | 0745667 A1 | 12/1996 |
| EP | 0903569 A1 | 3/1999 |
| EP | 1696238 A2 | 8/2006 |
| KR | 1020110044226 | 4/2011 |
| WO | 2005005045 A1 | 1/2005 |
| WO | 2010/009307 A2 | 1/2010 |
| WO | 2012048096 A2 | 4/2012 |
| WO | 2013045631 A1 | 4/2013 |
| WO | 2015078884 A1 | 6/2015 |
| WO | 2017212031 A1 | 12/2017 |
| WO | 2018030958 A1 | 2/2018 |

OTHER PUBLICATIONS

"Fast Wax Melting for Candle Making", BriskHeat.com, prior to Mar. 2018.

Kevin A. Heyries, "Megapixel Digital PCR", Nature Methods, vol. 8, No. 8, Aug. 2011, pp. 651-653.

* cited by examiner

INCUBATION WELL WITH AN UNVENTED GAS CAVITY FOR USE IN A MICROFLUIDIC CHIP

FIELD OF THE INVENTION

The field of the invention is the geometry of a single incubation segment in a microfluidic chip suitable for microbiological tests. Such tests include microbe identification and antimicrobial susceptibility testing (AST). Each segment may contain an antibiotic (or a combination of antibiotics) with a given concentration(-s). A single chip includes multiple incubation segments containing, for example, different antibiotics at different concentrations which allows antibiotic resistance to be detected and the determination of the minimum inhibitory concentration (MIC) for each of the antibiotics.

STATE OF THE ART

The patent application EP1696238 A2 discloses a chip for microbiological assays that includes multiple independent incubation segments in which bacterial culture takes place. These segments are outlet holes in a plastic plate manufactured using injection molding. Each segment is connected to a small air trap. With the proper orientation of the test card (i.e. during culturing of bacteria), the trap is located above the well where a sample compartment is placed. The trap is used to remove the gas bubbles from the suspension of bacteria that could disturb the optical measurement. However, it does not provide the appropriate access to the air necessary for bacterial growth. The chip must be closed with a permeable foil to enable culturing. The foil is specified in the patent application EP0745667 A1. To ensure the appropriate oxygen-permeability, the foil is made of oxygen-permeable polymethylpentene.

European patent EP 0903569 B1 describes a chip for microbiological assays that consists of three sections. The two external sections constitute the upper and lower walls of each incubation segment and the central element establishes the side walls. This design means that the chip needs to be made of transparent material (this applies to at least the external layers) so that the optical testing of a culture is possible in each segment. They have a circular section widening from the bottom to the top and they are connected together by vent channels with small cross-sections. When filling the incubation segments, the sample ejects the air inside the incubation segment via the ventilation duct. The small size of the duct allows the removal of the gas while preventing the inflow of the water sample. In the chip shown in the application US 2009/0155128 A1 air is removed from the incubation segments in a similar way.

WO2013/045631 A1 teaches unvented gas-filled chambers in which the gas is used to control the flow of a liquid from a distribution channel into the chamber (reducing the temperature of the gas in a chamber causes a drop in the pressure of the gas and draws the liquid into the chamber). The gas-filled chamber and the distribution channel are placed radially. This geometrical configuration does not provide gas exchange with the well where bacteria are being cultured and neither does it permit a dense distribution of chambers on the chip.

Therefore, in the state of the art there are no solutions where the incubation well on the chip for microbiological assays is connected with a gas cavity satisfying the need of cultured microorganisms for gas exchange, particularly for oxygen, in particular in a way that does not limit their growth. In the known chips, the air is removed from the incubation segment while it is filled, either outside its volume or to the special air trap. Providing the air to the bacteria through the network of microfluidic channels makes it impossible to ensure their physical separation, which otherwise could be achieved by filling the microfluidic channels with a mineral oil to counteract any cross-contamination. Another solution used is a special air-permeable foil. The described invention enables bacterial culturing in the incubation segments with the sealing of the chip with an impermeable foil.

OBJECT OF THE INVENTION

The object of the invention is to provide improved incubation segments for microbiological and similar assays.

This is achieved by an incubation segment having the features of claim 1. Further improvements are provided by the features of the dependent claims.

DETAILED DESCRIPTION OF INVENTION

In the following terms relating to position or orientation such as "upper", "lower", "horizontally", "vertically", "above" and "below" are in relation to the incubation segment when in its normal position of use. In the embodiment shown in the figures this normal position of use is where the surface of the chip containing the incubation segments is positioned with the outlet from the incubation well positioned below the inlet to the incubation well.

In the context of the present application, whenever "bacteria" are mentioned, the same applies to other microorganisms, such as e.g. single cell fungi.

Figure 1A:
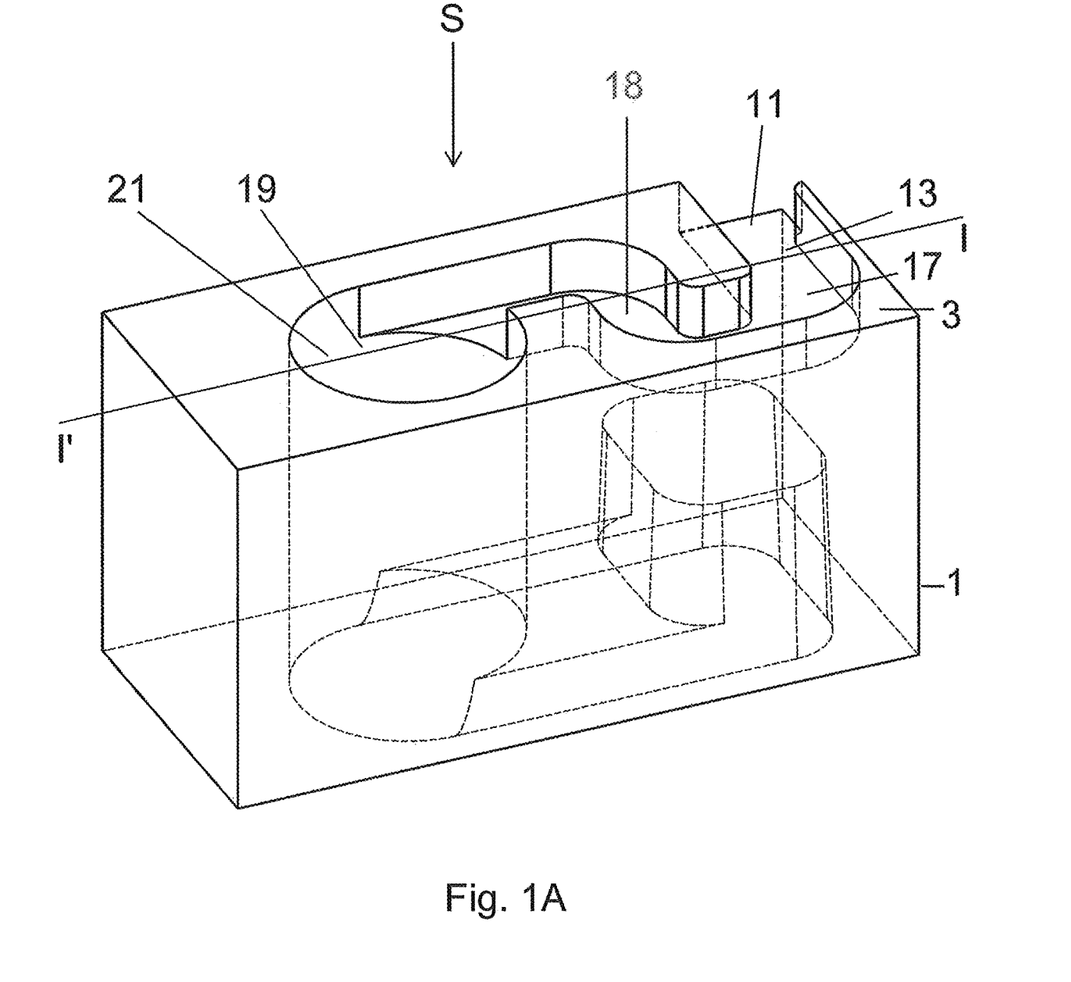
FIG. 1A shows an embodiment according to the present invention of an incubation segment from obliquely above when in use and FIG. 1B shows a view obliquely from below of the incubation segment when in use.
Figure 1B:
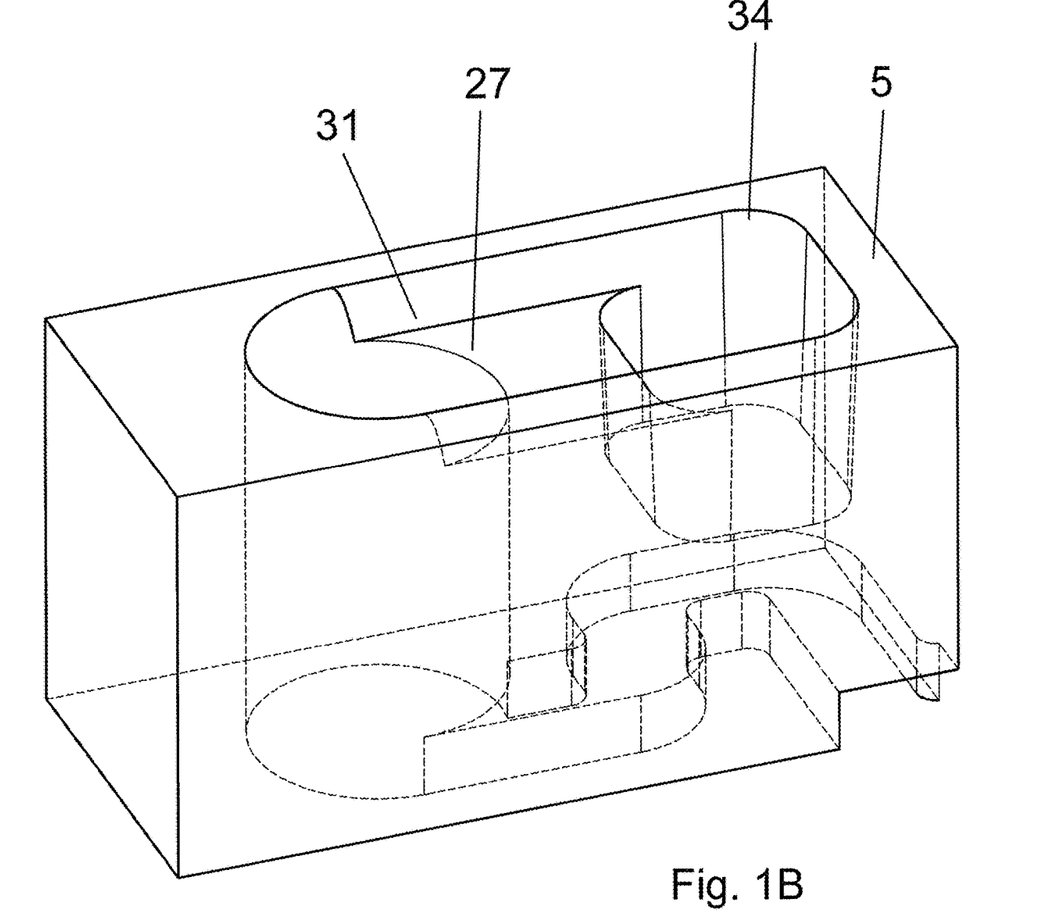
Figure 2:
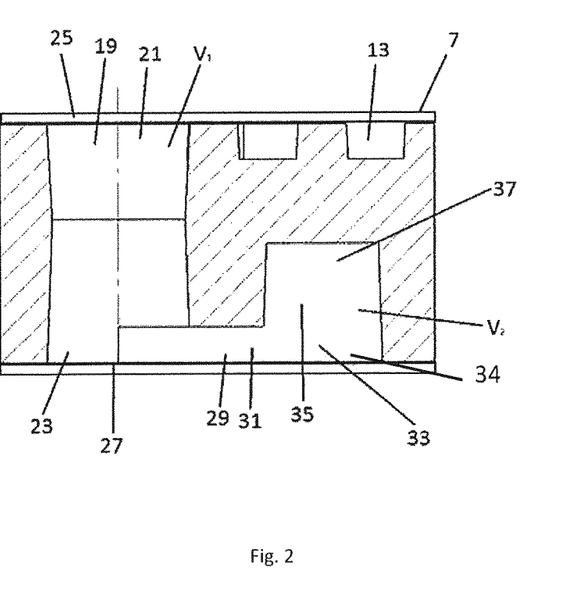
FIG. 2 shows the cross-section through line I-I' of FIG. 1A.

FIGS. 1A, 1B and 2 show schematically an example of an incubation segment S formed in a substrate 1 of preferably constant thickness. The substrate is preferably planar with an upper major face 3 and a, preferably parallel, lower face 5. The substrate may be made of any liquid and vapour impermeable material, for example a polymer, metal or glass. As shown in FIG. 2, the upper surface is covered by an upper layer 7 of impermeable, transparent material such as a polymer film and the lower major surface is covered by a lower layer 9 of impermeable, transparent material such as a polymer film. Inlet opening 11 leads to an inlet channel 13 for transporting a sample from the inlet opening to an incubation well. Alternatively, or additionally, an inlet opening may lead to a sample delivery channel (not shown) formed in the substrate. The inlet channel is preferably formed as a groove 17 in the major face. The inlet channel extends to, and opens out into, the side wall 19 of the upper end 25 of an incubation well 21. The incubation well is preferably in the form of a vertical through hole 23 extending though the substrate but not through the upper and lower layers of impermeable material. The incubation well is covered at its upper end 25 and lower end 27 by the respective upper and lower impermeable transparent films. At the lower end of the incubation well a, preferably horizontal, groove 29 formed in the lower face of the substrate forms a microfluidic communication channel 31, which may also be called a gas exchange channel, leading to, and opening into, the side wall 33 at the base 34 of an unvented gas cavity 35. The depth of the end of the groove where it enters the side wall of the gas cavity is a predetermined depth. The depth of the other end of the groove where it enters the incubation well may be less than, the same as, or greater than that predetermined depth. By "unvented gas cavity" it is meant that air or other fluids can only enter or leave the gas cavity via the communication channel during use. The gas cavity is in the form of a blind hole 37 of predetermined depth. The volume $V_t$ of the incubation well is greater than the volume $V_g$ of the gas cavity. The volume $V_c$ of the communication channel is preferably smaller than that of the gas cavity.

Figure 3:
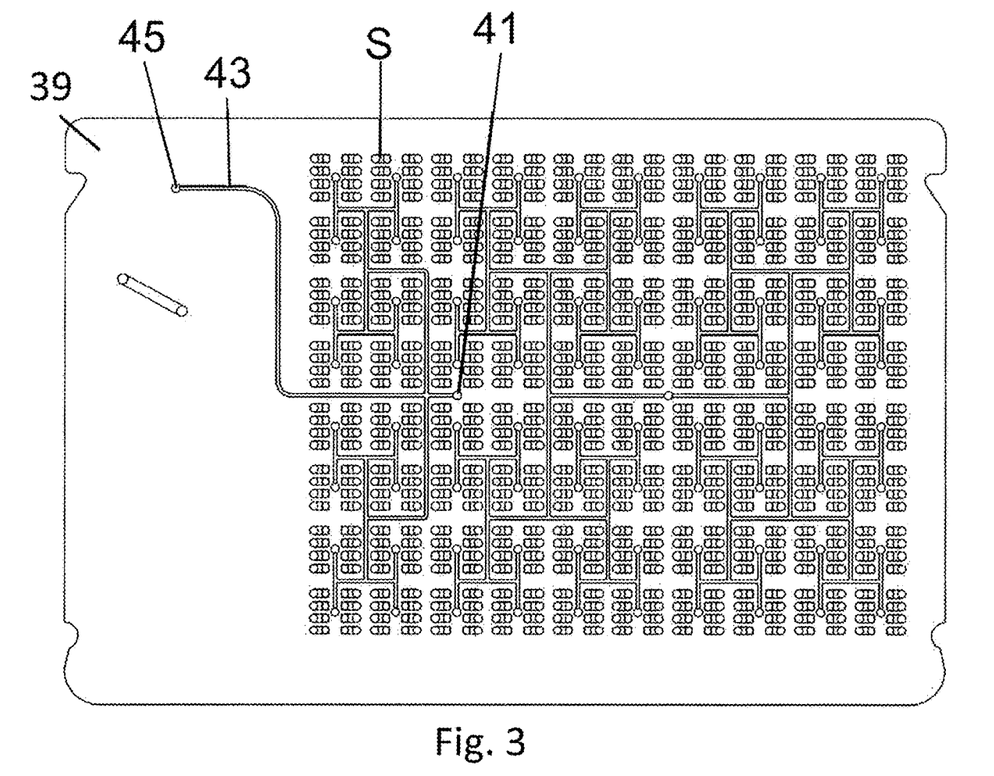
FIG. 3 shows schematically a plan view of one major side of a chip comprising a plurality of incubation segments according to the present invention.

Preferably a plurality of incubation segments S is formed as a network on a chip 39 as shown in FIG. 3. The chip may be provided with a network of sample delivery channels 41. These channels are connected to one or more sample input channels 43 which lead via a through hole 45 in the substrate to a sample reservoir. Preferably the network of channels is arranged in a fractal network which means that the distance that the sample travels to each incubation well from the sample reservoir is the same distance for each incubation segment. The shape of each incubation segment's inlet channel can be adapted, for example by being more or less curved, in order to aid in achieving this.

The incubation wells preferably contain different amounts of substances to be tested, for example antibiotics, and any other auxiliary substance and/or microbial growth indicators and any combination of these or any other reagents required to perform microbiological assays. These substances (collectively called "reagents" in the following) can be loaded into the incubation wells after attachment of one of the layers of impermeable transparent material and before the attachment of the second of the two layers of impermeable, transparent material. Preferably the reagents are attached to the walls of the incubation segment in a manner which allows them to be released when exposed to an aqueous solution.

The layers 7, 9 of impermeable transparent material (such as a polymer foil made of, for example preferably polystyrene, polycarbonate, poly(methyl methacrylate), cyclic olefin polymer or cyclic olefin copolymer) forms optical windows that enable illumination of the incubation well 21 and subsequent detection of scattered or fluorescent light. The gas cavity is preferably constructed such as to be open only from one side of the plate before attachment of the lower layer of impermeable, transparent material. Preferably, the gas cavity is located under the inlet channel 13 leading the sample to the incubation well and separated from the inlet channel by a predetermined thickness of substrate material. Having the inlet channel overlapping the gas cavity allows more efficient use of a space on the chip so that with chips of easily-handled sizes (e.g. 128 mm×85 mm), a large number of closely-spaced incubation segments (up to 640 or more) can be located on the chip which improves its functionality by allowing more bacterial cultures to be conducted during a single test. It should be noted that the number of the independent reaction wells is the main factor limiting a functionality of the prior art AST test cards. The possibility of accommodating such a large number of incubation segments on a single chip enables the acquisition of comprehensive information on the drug susceptibility of the bacteria in the sample (i.e. by permitting the testing of more antibiotics or their combinations for a possible resistance, determining of a true MIC which requires conducting a bigger number of cultures than determining the antibiotic concentration break points, possible finding of a resistance mechanism). In this respect the incubation segment enables obtaining unique properties which significantly exceed the properties of the AST test cards known in the state of the art.

The gas necessary for bacterial growth is contained in the gas cavity from where it diffuses to the suspension in the incubation well. With this solution, an impermeable foil can be used to seal the chip, which is less expensive than a permeable foil and provides a better protection against evaporation of the sample. The provision of air from the inside cavity of the incubation segment means that after a sample has been inputted in the incubation segment it is possible to seal the inlet opening and/or inlet channel. This can be achieved, for example, by inputting a non-aqueous liquid, such as a mineral oil, into the inlet opening. This prevents contamination between the segments and also prevents evaporation of the sample solution.

Figure 4:
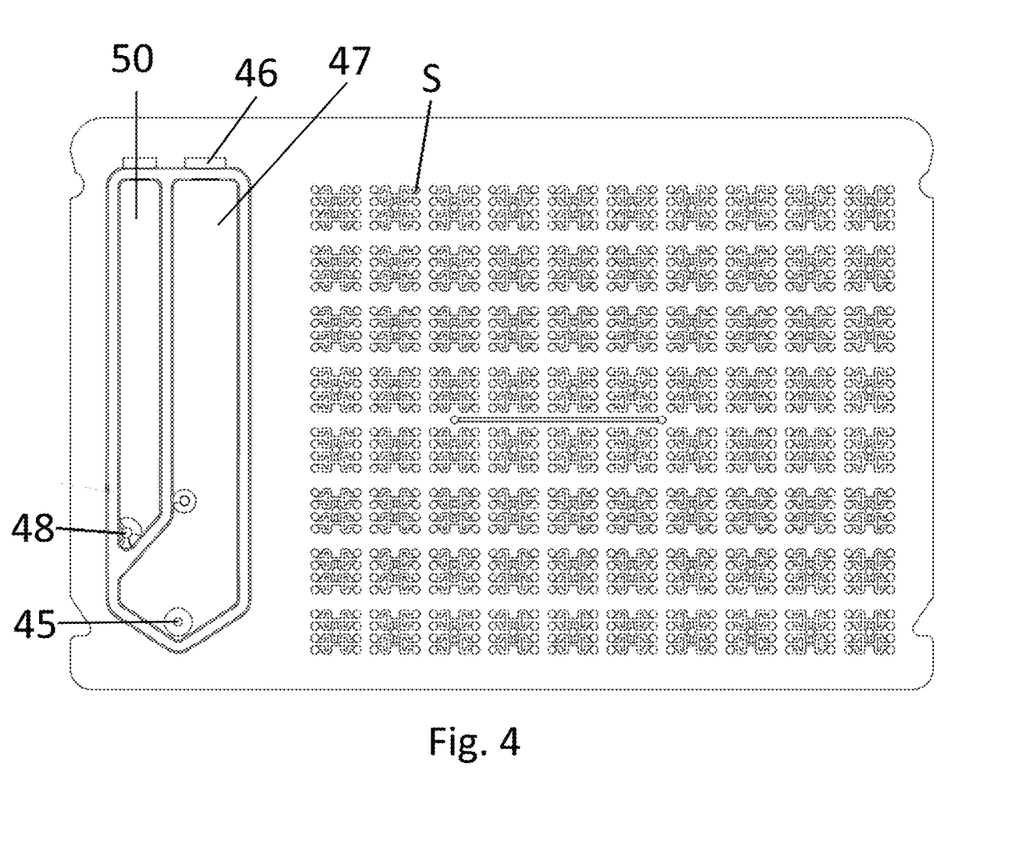
FIG. 4 shows schematically a plan view of the opposite major side of the chip of FIG. 3.

Chip 39 comprises a network of microfluidic channels 41 leading to the inlet openings of the incubation segments. When the chip is to be used and the incubation segments filled, a sample can be applied to the input end 43 of the network from the outlet 45 of a sample reservoir 47 previously loaded by an operator though an inlet port 46 in the sample reservoir. The sample flows via the network of microfluidic channels 41 from the sample reservoir to delivery channels which branch off from the main network of the microfluidic channels and each of which leads to the respective inlet opening of an incubation segment. Filling may be achieved by placing the chip, with a sample in its sample reservoir, in a sealed container such as a filling chamber and reducing the pressure in the chamber such that the chip is subjected to an atmosphere which is at a pressure below ambient atmospheric pressure thereby forming an under-pressure in the network of channels and incubation segments by way of the evacuation of air from the incubation segments and microfluidic channels through the sample in the sample reservoir and out of the chip. The pressure in the surrounding atmosphere (e.g. in the filling chamber) may subsequently be increased, thereby causing the movement of the sample from the sample reservoir to the incubation segments. The volume of the sample reservoir should be enough to ensure that the incubation wells each receive the correct dose of sample. Preferably the pressure is not increased to the ambient atmospheric pressure at this time, in order to allow the use of a further pressure increase to allow a sealing liquid, for example a non-aqueous liquid or an oil, to be applied to the network of microfluidic channels either from the outlet 48 of a non-aqueous liquid reservoir 50 via the sample reservoir or another route which sealing liquid, upon raising the external pressure to, for example, atmospheric pressure, is sucked into the inlet channels, thereby sealing the inlet channels. This prevents evaporation of the sample and cross-contamination between incubation segments.

In a further embodiment of the invention the positions of the inlet channel, the communication channel and gas cavity are inverted, i.e. the gas cavity is formed as a blind hole from the upper surface of the substrate, the communication channel is formed as a groove in the upper surface of the substrate and the inlet channel is formed as a groove in the lower surface of the substrate.

The volumes of individual sections in an incubation segment in an embodiment of an incubation segment in accordance with the invention are as follows:

Preferably, the volume of the gas cavity $V_g$ is greater than or equal to 5% of the volume $V_i$ of the incubation well and equal to or less than 100% of the volume $V_i$ of the incubation well, preferably equal to or less than 90% of the volume $V_i$ of the incubation well, more preferably equal to or less than 80% of the volume $V_i$ of the incubation well and most preferably is less than 70% of the volume $V_i$ of the incubation well, or the volume of the gas cavity $V_g$ is greater than or equal to 10% of the volume $V_i$ of the incubation well and equal to or less than 90% of the volume $V_i$ of the incubation well, preferably equal to or less than 70% of the volume $V_i$ of the incubation well, more preferably equal to or less than 50% of the volume $V_i$ of the incubation well and most preferably is less than 30% of the volume $V_i$ of the incubation well, or the volume of the gas cavity $V_g$ is greater than or equal to 20% of the volume $V_i$ of the incubation well and equal to or less than 70% of the volume $V_i$ of the incubation well, preferably equal to or less than 50% of the volume $V_i$ of the incubation well, more preferably equal to or less than 40% of the volume $V_i$ of the incubation well and most preferably is less than 30% of the volume $V_i$ of the incubation well.

The volume of the incubation well $V_i$ is preferably greater or equal to 0.5 μl and less than or equal to 5 μl, the volume of the gas cavity $V_g$ is preferably greater or equal to 0.5 μl and less than or equal to 1.5 μl, more preferably the volume of the incubation well $V_i$ is greater or equal to 1 μl and less than or equal to 2.5 μl, the volume of the gas cavity $V_g$ is preferably greater or equal to 0.7 μl and less than or equal to 1.3 μl; and, most preferably, the volume of the incubation well $V_i$ is greater or equal to 2.2 μl and less than or equal to 2.4 μl, the volume of the gas cavity $V_g$ is greater or equal to 0.9 μl and less than or equal to 1.2 μl.

The volume of the communication channel $V_c$ is preferably greater than or equal to 2% and less than or equal to 10% of the volume $V_i$ of the incubation well.

Preferably in all embodiments of the present invention, the smallest linear dimension of the incubation well, for example its diameter or width or linear distance from the communication channel to the inlet channel is equal to or less than 2 mm, preferably equal to or less than 1.5 mm, more preferably equal to or less than 1.0 mm, most preferably equal to or less than 0.5 mm.

The time needed to diffuse the oxygen through a culture medium layer with a given height has calculated and compared with the time in which the bacteria will consume the whole of the oxygen in the culture medium. These calculations are based on an example with an incubation well volume of 2.5 μl, and the following assumptions:

The simplest diffusion variant is considered where the particles diffuse the mean distance of x, which can be approximated with the equation $$t \approx \frac{x^2}{2D},$$

where D is the constant for the medium where diffusion takes place;

The amount of oxygen dissolved in the culture medium in the steady state is calculated based on Henry's law, according to which the oxygen concentration in the culture medium is directly proportional to its partial pressure (for the air present in the well, if not compressed, it is 0.22×1 atmospheres=0.22 atmospheres);

the bacteria will have access to enough oxygen to permit their growth when the time needed to diffuse the oxygen from the gas cavity to the culture medium is much shorter than the time in which the bacteria will consume the whole oxygen dissolved in the medium.

The time in which the bacteria will use all the oxygen collected in the gas cavity in a simplified case where the diffusion is immediate, has also been calculated.

In the simplest variant, the calculation determines how long it will take a given number of bacteria (expressed by OD or CFU/ml and the culture medium's volume) to consume the oxygen collected in the gas cavity (which has a given volume), by comparing the number of oxygen moles collected in the cavity and the oxygen consumption rate expressed in moles per minute, which is established based on literature. In the analyzed example, the data for *E. coli* was used, however the literature allows one to suppose that it is highly probable that it is the representative value for most bacteria, which is also justified by the Kleiber's Law. Additionally, to improve the estimation reliability, a consumption rate one order of magnitude greater than the value determined experimentally for *E. coli* was assumed for part of the calculations.

In a more complex case, the total oxygen consumption during bacterial growth was calculated, from the given OD or CFU/ml to a number of given times. It was assumed that the current oxygen consumption M at a given moment of time t can be calculated from the formula $M=k_{O_2}N_0 2^{t/g}$, where $N_0$ is the initial number of bacteria, $k_{O_2}$ is the constant corresponding to the oxygen consumption in moles per minute, and g is the constant corresponding to the time in which the number of bacteria is doubled. The total oxygen consumption can be then calculated by integration and for the end time T, expressed in minutes, it will be:

$$\int_0^T k_{O_2} N_0 2^{\frac{t}{g}} dt = \frac{k_{O_2} N_0 g}{\ln(2)} \left( 2^{\frac{T}{g}} - 2^{\frac{0}{g}} \right)$$

The table below shows the total oxygen consumption assuming that culturing starts with OD=0.001 in an incubation well with a volume of 2.5 μl and oxygen consumption of $$10^{-18} \frac{\text{mol}}{\text{CFU} \cdot s}.$$

A bacterium doubling time of 30 minutes was assumed and it was assumed that inhibition of bacterial growth occurred after exceeding $3.3 \times 10^9$ CFU/ml. Because of the estimation of the maximum consumption, it was also assumed that the oxygen consumption does not drop when the maximum number of bacteria is reached.

| Time [h] | OD | CFU/ml | Total oxygen consumption [mol] | Minimum required volume of gas cavity [μl] |
|---|---|---|---|---|
| 0 | 0.001 | 8.00E+05 | — | — |
| 2 | 0.02 | 1.28E+07 | 7.79E−11 | 1.66E−05 |
| 4 | 0.26 | 2.05E+08 | 1.32E−09 | 2.82E−04 |
| 6 | 4.1 | 3.28E+09 | 2.13E−08 | 4.52E−03 |

-continued

| Time [h] | OD | CFU/ml | Total oxygen consumption [mol] | Minimum required volume of gas cavity [µl] |
|---|---|---|---|---|
| 12 | 4.1 | 3.28E+09 | 3.76E−07 | 0.08 |
| 18 | 4.1 | 3.28E+09 | 7.30E−07 | 0.16 |
| 24 | 4.1 | 3.28E+09 | 1.08E−06 | 0.23 |

The above data indicate that with a test cycle of 24 hours the required volume of gas cavity is low and does not considerably restrict the bacterial growth. Furthermore even lower volume is needed to reach a maximum possible concentration of bacteria which is the last moment giving relevant information about bacterial growth i.e. later processes in the incubation well are not important for microbe identification or AST assays with the use of the incubation segment according to the present invention. For the well with a volume of 2.5 µl at atmospheric pressure, the factor limiting bacterial growth can be the diffusion time which can become meaningful from ca. $1.4 \times 10^5$ CFU (which corresponds to OD 0.07 and $5.6 \times 10^7$ CFU/ml), if one assumes that this time should be shorter by one order of magnitude than the oxygen consumption time. This may be the case despite the high reserve of oxygen in the air of the gas cavity. Given that the diffusion time is proportional to the square of the distance, the culture medium layer should be made as thin as possible.

In order to avoid limiting gas diffusion in all embodiments of the present invention, preferably the length of the communication channel from the gas cavity to the incubation well is less than 0.5 mm, more preferably, less than 0.4 mm, even more preferably equal to or less than 0.3 mm and most preferably equal to or less than 0.2 mm.

Increase of the air pressure in the chip will allow more oxygen to be diffused into the culture medium which will also improve the efficiency of bacteria feeding. For example, at a pressure of 10 bars, 10 times more oxygen as compared to the atmospheric pressure would be sent to the medium at any time.

One aspect of the present invention relates to an isolate of bacteria being introduced in suspension to a sample reservoir on the chip. The suspension of bacteria is forced to flow into the incubation segments, each of them having previously been supplied with antibiotic in a dry form (for example, with different types of antibiotics in various amounts) and possible auxiliary substance and/or bacterial growth indicators and any combination of these or any other reagents required to perform microbiological assays. After filling the incubation wells with a sample, these antibiotics and substances are dissolved in the sample.

The properties of the incubation segment allow for proper functionality during drug susceptibility testing or other such microbiological assays i.e. the incubation segment allows the cultivation of the bacteria and repeated optical measurements to detect their potential growth. In particular the incubation segment: (1) enables gas exchange so that it is not a factor limiting the bacterial population growth rate and (2) provides an appropriately long and undisturbed optical path for optical investigation.

The chip containing the incubation segments should be sufficiently airtight to protect the sample from leaking or spilling and evaporation during a test.

The invention claimed is:

1. An incubation segment for use in a microfluidic chip for microbiological assays, wherein said incubation segment is formed in a substrate with a first major face and a second major face, said segment comprises an incubation well, an inlet channel through which a sample may be inputted into said incubation well, and a gas cavity connected to said incubation well by a microfluidic communication channel, wherein said gas cavity is unvented and a base of the gas cavity is connected to a base of the incubation well by the communication channel, wherein the incubation well comprises an optical window, the optical window comprising a through hole extending from said first major face through said substrate to said second major face, a first impermeable, transparent layer covering the incubation well on said first major face, and a second impermeable, transparent layer covering the incubation well on said second major face.

2. The incubation segment of claim 1, wherein the volume of the incubation well $V_i$ is 0.5 µl to 5 µl, the volume of the gas cavity Vg is 0.5 µl to 1.5 µl.

3. The incubation segment of claim 2, wherein the volume of the incubation well $V_i$ is 1 µl to 2.5 µl, the volume of the gas cavity Vg is 0.7 µl to 1.3 µl.

4. The incubation segment of claim 3, wherein the volume of the incubation well $V_i$ is 2.2 µl to 2.4 µl, the volume of the gas cavity $V_g$ is 0.9 µl to 1.2 µl.

5. The incubation segment of claim 1, wherein the volume of the gas cavity $V_g$ is 5% to 100% of the volume $V_i$ of the incubation well.

6. The incubation segment of claim 1, wherein the volume of the gas cavity $V_g$ is equal to or less than 90% of the volume $V_i$ of the incubation well.

7. The incubation segment of claim 1, wherein the volume of the gas cavity $V_g$ is equal to or less than 70% of the volume $V_i$ of the incubation well.

8. The incubation segment of claim 1, wherein the volume of the gas cavity $V_g$ is greater than or equal to 10% of the volume $V_i$ of the incubation well and equal to or less than 90% of the volume $V_i$ of the incubation well.

9. The incubation segment of claim 1, wherein the volume of the gas cavity $V_g$ is 10% to 30% of the volume $V_i$ of the incubation well.

10. The incubation segment of claim 1, wherein a smallest linear dimension of the incubation well is equal to or less than 2 mm.

11. The incubation segment of claim 1 wherein a smallest linear dimension of the incubation well is equal to or less than 0.5 mm.

12. The incubation segment of claim 1, wherein the length of the communication channel is less than 0.5 mm.

13. The incubation segment of claim 9, wherein the length of the communication channel is less than 0.2 mm.

14. The incubation segment of claim 1, wherein the gas cavity is formed as a blind hole in said second major face of said substrate.

15. The incubation segment of claim 1, wherein the volume of the communication channel $V_c$ is 2% to 10% of the volume $V_i$ of the incubation well.

16. A microfluidic chip for microbiological assays, the chip comprising a plurality of incubation segments of claim 1.

17. The microfluidic chip of claim 16, wherein the substrate is made of a polymer.

18. The microfluidic chip of claim 17, wherein the polymer is selected from a group consisting of polystyrene, polycarbonate, poly(methyl methacrylate), cyclic olefin polymer or cyclic olefin copolymer.

19. The microfluidic chip of claim 16, wherein the first impermeable, transparent layer and the second impermeable, transparent layer comprise the same material.

20. The incubation segment of claim 1, wherein the inlet channel is formed as a groove in the first major face of the substrate.

21. The incubation segment of claim 1, wherein the inlet channel is formed as a groove in the first major face of the substrate and the gas cavity is defined in the second major face.

22. The incubation segment of claim 21, wherein the gas cavity at least partially overlaps with the inlet channel.

23. The incubation segment of claim 1, wherein the transparent layers enable illumination and detection of scattered or fluorescent light.

24. The incubation segment of claim 1 containing antibiotics.

25. The chip of claim 16, wherein the substrate is made of liquid and vapour impermeable material.

* * * * *